United States Patent [19]

Bailey

[11] Patent Number: 5,808,085
[45] Date of Patent: Sep. 15, 1998

[54] STEREOSELECTIVE PREPARATION OF 2-SUBSTITUTED SUCCINIC ACID DERIVATIVES

[75] Inventor: Murray Douglas Bailey, Pierrefonds, Canada

[73] Assignee: Boehringer Ingelheim (Canada) Ltd., Quebec, Canada

[21] Appl. No.: 767,917

[22] Filed: Dec. 17, 1996

[30] Foreign Application Priority Data

Dec. 22, 1995 [CA] Canada ................................ 2165996

[51] Int. Cl.$^6$ .................. C07D 277/20; C07C 19/01; C07C 19/075
[52] U.S. Cl. ................... 548/192; 548/194; 560/183
[58] Field of Search ................... 560/183; 548/192, 548/194

[56] References Cited

U.S. PATENT DOCUMENTS

| | | | |
|---|---|---|---|
| 5,215,918 | 6/1993 | Muchmore | 435/180 |
| 5,275,950 | 1/1994 | Dickman | 435/280 |

FOREIGN PATENT DOCUMENTS

| | | |
|---|---|---|
| 0589445 | 3/1994 | European Pat. Off. . |
| 9504043 | 2/1995 | WIPO . |

OTHER PUBLICATIONS

*Tetrahedron: Asymmetry* vol. 6, No. 2, pp. 381–384, 1995; "Resolution of 2–Azol–1–ylsuccinic Esters by Enantioselective Inclusion Methodology", P. Zaderenko et al.
*Tetrahedron: Asymmetry* vol. 4, No. 5, pp. 783–792, 1993, "Enzymatic Resolution of 3–Substituted–4–oxoesters", L. Blanco et al.
*Synlett,* 1993, pp. 155–157, "Short and Efficient Large Scale Synthesis of (R)–2–Benzyluccinic Acid 4–[4–(BOC–amino)–1–piperidide]Monoamide: N–Terminal Component of Renin Inhibitors of Asymmetric Hydrogenation", H. Jendralla et al.
*Tetrahedron Letters,* vol. 34, No. 28, pp. 4485–4488, 1993, "N–(Boc)–L–(2–Bromoallyl)–Glycine: A Versatile Intermediate for the Synthesis of Optically Active Unnatural Amino Acids", M. R. Leanna et al.
*Tetrahedron Letters,* vol. 34, No. 28, pp. 4485–4488, 1993, "Enzyme–Catalyzed Synthesis of Optically Pure Beta–Sulfonamidopropionic Acids. Useful Starting Materials for P–3 Site Modified Renin Inhibitors", H. Mazdiyasni et al.

*J. Chem. Soc. Perkin Trans,* 1, 1990, pp. 1441–1445, "Asymmetric Synthesis of (R)–and (S)–4–(Substituted Benzyl)dihydrofuran–2(3H)–ones: An Application of theRuthenium–binap+Complex–catalysed Asymmetric Hydrogenation ofAlkylidenesuccinic Acids", L. Shao et al.

*Journal of the American Chemical Society,* 90:13, Jun. 19, 1968, pp. 3495–3502, "Absolute Steric Course of Hydrolysis by α–Chymotrypsin. Esters of α–Benzylsuccinic, α–Methyl–β–phenylpropionic, and α–Methylsuccinic Acids", S.G. Cohen and A. Milovanovic.

*Primary Examiner*—Zinna Northington Davis
*Attorney, Agent, or Firm*—R. P. Raymond; M-E. M. Devlin; A. R. Stempel

[57] ABSTRACT

A highly efficient and practical means has been developed which enables compounds of the formula:

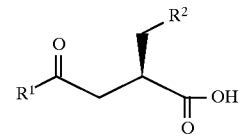

wherein $R^1$ is lower alkoxy, lower alkylamino, di-(loweralkyl) amino, or the monovalent radical A—$NR^3$, wherein A is lower alkyl or A is $R^4R^5NC(O)CH_2$ wherein, for example, $R^4$ is hydrogen or alkyl and $R^5$ is hydrogen, alkyl or a substituted alkyl, or $R^5$ is $R^6R^7$N-Alk wherein $R^6$ and $R^7$ each is hydrogen or lower alkyl and Alk is a divalent alkyl radical; $R^3$ is, for example, benzyl, alkyl or a substituted alkyl; and $R^2$ is, inter alia, alkyl, cycloalkyl, 1H-imidazol-4-yl, 4-thiazolyl or 2-amino-4-thiazolyl; to be prepared through the kinetic resolution of a compound of the formula:

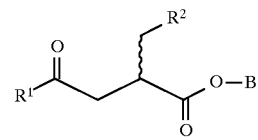

wherein $R^1$ is as defined herein, $R^2$ is as defined herein, and B is lower alkyl. These compounds are useful intermediates in the synthesis of renin inhibiting compounds.

11 Claims, No Drawings

STEREOSELECTIVE PREPARATION OF 2-SUBSTITUTED SUCCINIC ACID DERIVATIVES

FIELD OF THE INVENTION

This invention relates to renin inhibiting compounds. More specifically, this invention relates to a process for the preparation of compounds with high enantiomeric purity which are useful intermediates in the synthesis of renin inhibiting compounds, and to the compounds with high enantiomeric purity prepared by this process.

BACKGROUND OF THE INVENTION

Compounds which inhibit the enzyme renin, an aspartyl protease which cleaves angiotensinogen to AI, have been the subject of much research interest in recent years, and a great deal of effort has been devoted to designing renin inhibitors which mimic the natural renin substrate angiotensinogen. Much of this effort has been focused on the design of analogous substrates incorporating therein a non-cleavable mimic (i.e. a transition state analog) of the renin cleavage site (i.e. Leu-Val) of human angiotensinogen. As a result, a number of potent renin inhibitors have been identified in the laboratory, and the ability of renin inhibitors to lower blood pressure and to reduce plasma renin activity has now been demonstrated in the clinic (for a recent review on renin inhibitors, see W. J. Greenlee, Medical Research Reviews 1990, 10, 173). Renin inhibiting compounds which have been found to be of particular interest are the compounds of formula I:

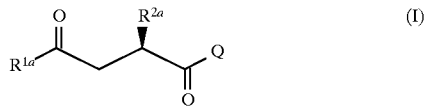

wherein $R^{1a}$ is A—$NR^3$, wherein A is $R^4R^5NC(O)CH_2$ wherein, for example, $R^4$ is hydrogen or alkyl and $R^5$ is hydrogen, alkyl or a substituted alkyl such as 2-(2-pyridinyl) ethyl, or $R^4$ and $R^5$ together with the nitrogen atom to which they are attached form a pyrrolidino, piperidino, morpholino or thiomorpholino; $R^3$ is, for example, benzyl, alkyl or a substituted alkyl such as cyclohexylmethyl; $R^2a$ is, for example, alkyl, cycloalkyl, 1H-imidazol-4-yl, 4-thiazolyl or 2-amino-4-thiazolyl; and Q is a renin substrate transition state analog, for example, 1(S)-(2-methylpropyl)-2(S)-hydroxy-5-methylhexylamino, 1(S)-(cyclohexylmethyl)-2 (S)-hydroxy-5-methylhexylamino, 1(S)-{(4-methoxylphenyl)methyl}-2(S)-hydroxy-5-methylhexylamino, 1(S)-(cyclohexylmethyl)-2(S)-hydroxy-4-methylpentylamino, 1(5)-(cyclohexylmethyl)-2(S)-hydroxy-3-cyclopropylpropylamino, 1(S)-(2-methylpropyl)-2(R),3(S)-dihydroxy-5-methylhexylamino, 1(S)-(cyclohexylmethyl)-2(R),3(S)-dihydroxy-5-methylhexylamino, 1(S)-{(4-methoxyphenyl)methyl}-2(R), 3(S)-dihydroxy-5-methylhexylamino, 1(S)-(2-methylpropyl)-2(R),3(S)-dihydroxy-3-cyclopropylpropylamino, 1(S)-(cyclohexylmethyl)-2(R),3 (S)-dihydroxy-3-cyclopropylpropylamino, 1(S)-(phenylmethyl)-2(R), 3(S)-dihydroxy-3-cyclopropylpropylamino, 1(S)-{(4-methoxyphenyl)methyl}-2(R),3(S)-dihydroxy-3-cyclopropylpropylamino, 1(S)-(cyclohexylmethyl)-2(R)-hydroxy-3-(1-methylethoxy)-3-oxopropylamino or 1(S)-(cyclohexylmethyl)-2(S)-hydroxy-2-(1,5,5-trimethyl-2-oxopyrrolidin-3(S)-yl)ethylamino; or a therapeutically acceptable acid addition salt thereof.

A renin inhibiting compound of most interest is the compound of formula Ia:

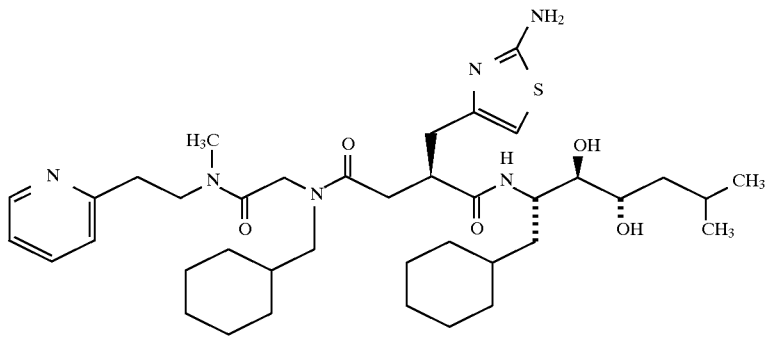

The central portion of three renin inhibiting compounds is a chiral succinoyl derivative with an (R)-configuration. The original synthesis of the compounds of formula I and Ia employed succinoyl intermediates derived from an asymmetric synthesis utilizing Evans' chiral auxiliary chemistry to introduce the chiral center with the proper configuration (Lavallée et al., European Patent application EP 589445, published Mar. 30, 1994). This methodology employs expensive chiral auxiliaries, as well as several cryogenic steps, making this last procedure difficult for the large scale preparations of these compounds. Therefore, efficient and low cost methods which are amenable to scale-up are needed for the preparation of intermediates useful for the preparation of compounds of formula I and Ia.

The preparation of compounds with high enantiomeric purity has been reported previously, for example:

R. W. Dugger, PCT patent application WO 95/04043, published Feb. 9, 1995

D. A. Dickman et al., U.S. Pat. No. 5,275,950, issued Jan. 4, 1995

P. Zaderenko et al., Tetrahedron:Asymmetry 1995, 6, 381

L. Blanco et al., Tetrahedron:Asymmetry 1993, 4, 783

H. Jendralla et al., SYNLETT 1993, 155

M. R. Leanna et al., Tetrahedron Letters 1993, 34, 4485

H. Mazdiyasni et al., Tetrahedron Letters 1993, 34, 435

L. Shao et al., J. CHEM. SOC. PERKIN TRANS. 1 1990, 1441

S. G. Cohen et al., J. Am. Chem. Soc. 1968, 90, 3495

The present process and compounds prepared by the present process can be distinguished readily from the prior art. The compounds prepared by the present process possess a different chemical structure than those in the prior art, and can be used as intermediates in the preparation of renin inhibiting compounds of formula I and Ia.

SUMMARY OF THE INVENTION

In accordance with the present invention, there is disclosed a process for the preparation of renin inhibiting compounds of formula I and Ia, as well as intermediates useful for the preparation of renin inhibiting compounds of formula I and Ia.

In particular, the present invention relates to a process for the preparation of compounds with high enantiomeric purity of formula II:

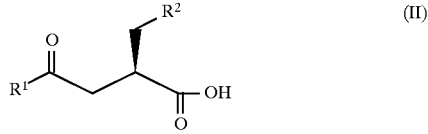

wherein $R^1$ is lower alkoxy, lower alkylamino, di(lower alkyl)amino or $R^1$ is A—$NR^3$, wherein A is lower alkyl $R^4R^5NC(O)CH_2$ wherein, (a) $R^4$ is hydrogen or lower alkyl and $R^5$ is hydrogen, lower alkyl or lower alkyl monosubstituted with lower cycloalkyl, phenyl, or a heterocylic ring (hereinafter designated as "Het") which is an unsubstituted, mono-substituted or disubstituted, five- or six-membered ring containing one or two heteroatoms selected from the group consisting of N, O and S, and wherein each substituent is selected independently from the group consisting of lower alkyl, lower alkoxy, halo, amino or lower alkylamino; or (b) $R^4$ is lower alkyl and $R^5$ is $R^6R^7N$-Alk wherein $R^6$ and $R^7$ each is hydrogen or lower alkyl and Alk is a divalent alkyl radical derived by the removal of two hydrogen atoms of a straight or branched chain hydrocarbon containing from one to six carbon atoms; or (c) $R^4$ is lower alkyl and $R^5$ is lower alkoxy; or (d) $R^4$ and $R^5$ together with the nitrogen atom to which they are attached form a pyrrolidino, piperidino, 4-{(lower alkoxy)-(lower alkoxy)}-1-piperidinyl, morpholino or thiomorpholino;

$R^3$ is lower alkyl or lower alkyl monosubstituted with lower cycloalkyl, phenyl, 4-(lower alkyl)phenyl, 4-(lower alkoxy)phenyl, 4-halophenyl, 3,4-methylenedioxyphenyl, 1-naphthyl, 2-naphthyl or Het wherein Het is as defined herein; and $R^2$ is lower alkyl, CCl=$CH_2$, CBr=$CH_2$, lower cycloalkyl, 2-amino-4-thiazolyl, 2-(amino protecting group)amino-4-thiazolyl or Het wherein Het is as defined herein, said process comprising:

(i) selectively hydrolyzing one enantiomer of a racemic mixture of an ester of formula III:

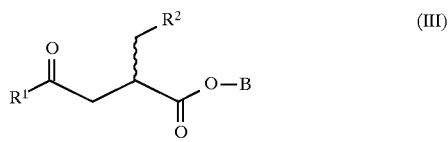

wherein $R^1$ is as defined herein, $R^2$ is as defined herein, and B is lower alkyl, with an effective amount of an esterase selected from Subtilisin Carlsberg or α-chymotrypsin, in a reaction medium comprising $H_2O$ or a mixture of $H_2O$ and an $H_2O$ miscible inert organic solvent, in the presence of an alkali metal hydroxide to maintain the pH of the medium at about 7.0–8.5, to form a reaction mixture containing compounds of formula II (as an alkali metal salt) and IIIa:

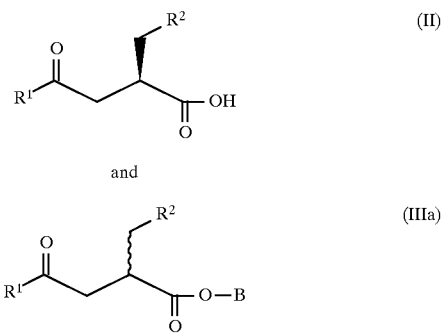

and (ii) separating from the mixture resulting from step (i) the compound of formula II.

In a preferred process for the preparation of compounds of formula II, the ester of formula III is selected from the group of compounds represented by formula III wherein $R^1$ is lower alkoxy, lower alkylamino, di(lower alkyl)amino or $R^1$ is A—$NR^3$, wherein A is $R^4R^5NC(O)CH_2$ wherein $R^4$ is methyl and $R^5$ is methyl, 2-(2-pyridinyl)ethyl or 2-(3-pyridinyl)ethyl; $R^3$ is 1-ethylpropyl, cyclopentylmethyl, cyclohexylmethyl, 1(S)-cyclohexylethyl, cycloheptylmethyl, phenylmethyl, 1(S)-phenylethyl, (1-methylcyclohexyl)methyl; $R^2$ is CCl=$CH_2$, CBr=$CH_2$, 2-amino-4-thiazolyl, 2-(amino protecting group)amino-4-thiazolyl or a five-membered heterocyclic ring containing one or two heteroatoms selected from the group consisting of N, O and S; and B is methyl or ethyl. Most preferably, $R^1$ is 1,1-dimethylethoxy or the monovalent radical:

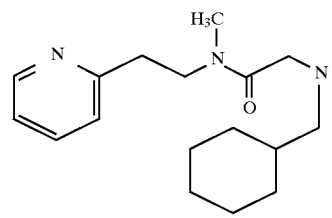

$R^2$ is CCl=$CH_2$, CBr=$CH_2$, or 2-amino-4-thiazolyl, and B is methyl.

The process of the instant invention is preferably carried out at a temperature of 20° to 55° C., more preferably at a temperature of 20° to 37° C. The alkali metal hydroxide used in the instant process is preferably selected from NaOH, KOH and LiOH, and is added to the reaction mixture in a sufficient amount to maintain the pH of the reaction at about 7.0 to 8.5, more preferably 7.0 to 8.0. The process of the instant invention is carried out in $H_2O$ or a mixture of $H_2O$ and an $H_2O$ miscible inert organic solvent, preferably in $H_2O$ or a mixture of $H_2O$ and 0 to 30% (v/v) of an $H_2O$ miscible inert organic solvent. The inert organic solvent is preferably selected from acetone or acetonitrile.

This invention also relates to compounds of formula II wherein $R^1$ and $R^2$ are as defined herein. The compounds of formula II prepared by the instant process can be subjected to standard transformations as disclosed by Lavallée et al., European Patent application EP 589445, published Mar. 30, 1994, to prepare renin inhibiting compounds of formula I and Ia.

DETAILS OF THE INVENTION

General

With reference to the instances where (R) or (S) is used to designate the configuration of a radical, e.g. $R^2$ of the compound of formula I, the designation is done in the context of the compound and not in the context of the radical alone.

The term "halo" as used herein means a halo radical selected from bromo, chloro, fluoro or iodo.

The term "lower alkyl" as used herein, either alone or in combination with another radical, means straight chain alkyl radicals containing one to four carbon atoms and branched chain alkyl radicals containing three to four carbon atoms and includes methyl, ethyl, propyl, butyl, 1-methylethyl, 1-methylpropyl, 2-methylpropyl and 1,1-dimethylethyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy.

The term "lower cycloalkyl" as used herein, either alone or in combination with another radical, means saturated cyclic hydrocarbon radicals containing from three to seven carbon atoms and includes cyclopropyl, cyclobutyl, cyclopentyl, cyclohexyl and cycloheptyl.

The term "Het" as used herein means a monovalent radical derived by removal of a hydrogen from a five- or six-membered saturated or unsaturated heterocycle containing from one to two heteroatoms selected from nitrogen, oxygen and sulfur. Optionally, the heterocycle may bear one or two substituents; for example, N-oxido, lower alkyl, lower alkoxy, halo, amino or lower alkylamino. Examples of suitable heterocycles and optionally substituted heterocycles include pyrrolidine, tetrahydrofuran, thiazolidine, pyrrole, 1H-imidazole, 1-methyl-1H-imidazole, pyrazole, furan, thiophene, oxazole, isoxazole, thiazole, 2-methylthiazole, 2-aminothiazole, 2-(methylamino)thiazole, piperidine, 1-methylpiperazine, 1,4-dioxane, morpholine, pyridine, pyridine N-oxide, pyrimidine and 2,4-dimethylpyrimidine.

The term "amino" as used herein means an amino radical of formula $-NH_2$. The term "lower alkylamino" as used herein means alkylamino radicals containing one to six carbon atoms and includes methylamino, propylamino, (1-methylethyl)amino and (2-methylbutyl)amino. The term "di(lower alkyl)amino" means an amino radical having two lower alkyl substituents each of which contains one to six carbon atoms and includes dimethylamino, diethylamino, ethylmethylamino and the like.

The term "amino protecting group" as used herein means a group intended to protect an amino group or the N-terminus of an amino acid against undesirable reactions during synthetic procedures. Commonly used amino protecting groups are disclosed in general textbooks of peptide chemistry; for instance, "The Peptides: Analysis, Synthesis, Biology", E. Gross et al., Eds., Academic Press, New York, N.Y., USA, 1979–1987, Volumes 1 to 9, and M. Bodanszky, "Peptide Chemistry", 2nd rev ed, Springer-Verlag, Berlin, Germany, 1993. Examples of amino protecting groups include benzyloxycarbonyl, 4-methoxybenzyloxycarbonyl or 2,2,2-trichloroethoxycarbonyl and 1,1-dimethylethoxycarbonyl.

The term "high enantiomeric purity" as used herein refer to a compound having at least 75% enantiomeric excess (ee) of one enantiomer, preferably at least 85% ee, more preferably at least 95% ee and most preferably at least 99% ee.

Process for Preparing the Compounds of Formula 1

Racemic mixtures of compounds of formula III, which are used in the synthesis of compounds of formula II, can be prepared by a variety of processes involving known methods. Description of the methods are found in standard textbooks such as "Annual Reports In Organic Synthesis-1994", P. M. Weintraub et al., Eds., Academic Press, Inc., San Diego, Calif., USA, 1994 (and the preceding annual reports), "Vogel's Textbook of Practical Organic Chemistry", B. S. Furniss et al., Eds., Longman Group Limited, Essex, UK, 1986, and "Comprehensive Organic Synthesis", B. M. Trost and I. Fleming, Eds., Pergaman Press, Oxford, UK, 1991, Volumes 1 to 8.

A general procedure for the preparation of compounds with high enantiomeric purity of formula II, which are useful intermediates in the synthesis inhibiting compounds of formula I and Ia, is outlined in scheme 1.

Scheme 1

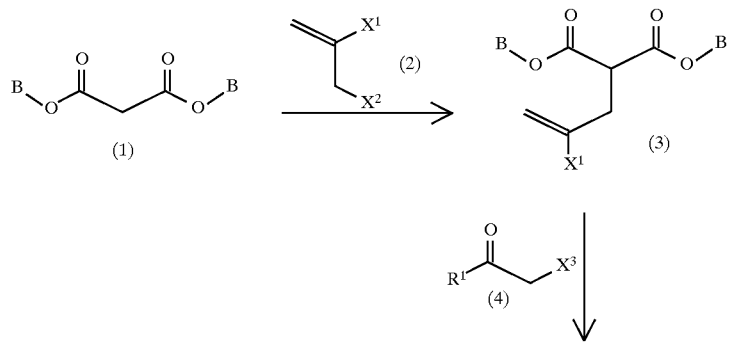

-continued
Scheme 1

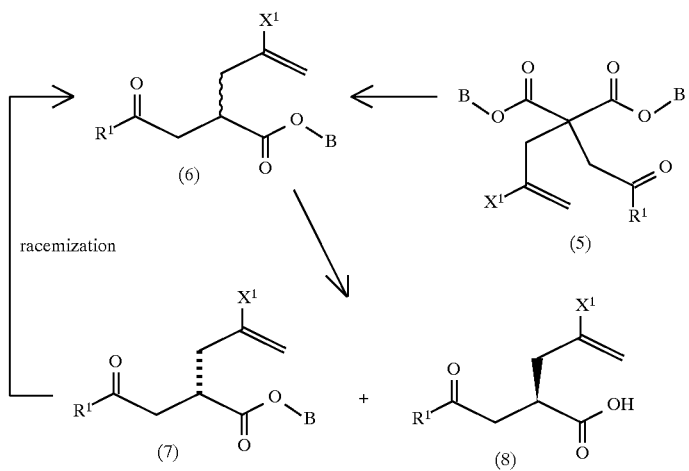

According to scheme 1, a mixture of malonate (1), wherein B is lower alkyl, and 2,3-disubstituted propene (2), wherein $X^1$ and $X^2$ are selected from Br, Cl or I, in an inert solvent (for example MeOH, THF and the like) at a temperature of from about 0° C. to 100° C. is treated with a base (for example NaOMe when the solvent is MeOH, or NaH, NaHMDS or potassium tert-butoxide when the solvent is THF, and the like), to give the corresponding mono-alkylated malonate derivative of formula 3. The mono-alkylated malonate derivative of formula 3 is reacted with the compound of formula 4, wherein $X^3$ is selected from Br, Cl or I, and $R^1$ is as defined herein, in the presence of base (for example NaOH, NaH, KOtBu and the like) to give the corresponding di-alkylated malonate derivative of formula 5. Selective monosaponification of the dialkylated malonate of formula 5 by treatment with an aqueous base (for example KOH, LiOH, NaOH and the like) in a mixture of $H_2O$ and an $H_2O$ miscible inert solvent (for example, THF/$H_2O$ MeOH, MeOH/$H_2O$, and the like), followed by acidification and then refluxing in toluene and the like to induce decarboxylation gives the corresponding racemic succinyl derivative of formula 6. Treatment of the racemic succinyl derivative of formula 6 with an esterase (for example, Subtilisin Carlsberg or α-chymotrypsin) in either $H_2O$ or a mixture of $H_2O$ and a $H_2O$ miscible solvent (for example, acetone and the like) in the presence of an alkali metal hydroxide (for example, NaOH, KOH, LiOH and the like) to maintain the pH at about 7 to 8.5, gives a mixture of the corresponding enantiomers of formula 7 and 8. The unreacted (R)-ester of formula 7 is extracted from the mixture of the enantiomers of formula 7 and 8 with an organic solvent (for example, EtOAc and the like). The (R)-ester of formula 7 can be recycled by racemization under basic conditions to give the corresponding racemic succinyl derivative of formula 6. The (S)-acid of formula 8 is recovered by acidifying the aqueous phase and then extracting with an organic solvent (for example, EtOAc and the like). By using procedures disclosed by Lavallée et al. (EP 589445, published Mar. 30, 1994), the (S)-acid of formula 8, which is a compound of formula II, prepared in this manner can be used directly in the preparation of renin inhibiting compounds of formula I and Ia.

Another general procedure for the preparation of compounds of formula II is outlined in scheme 2.

Scheme 2

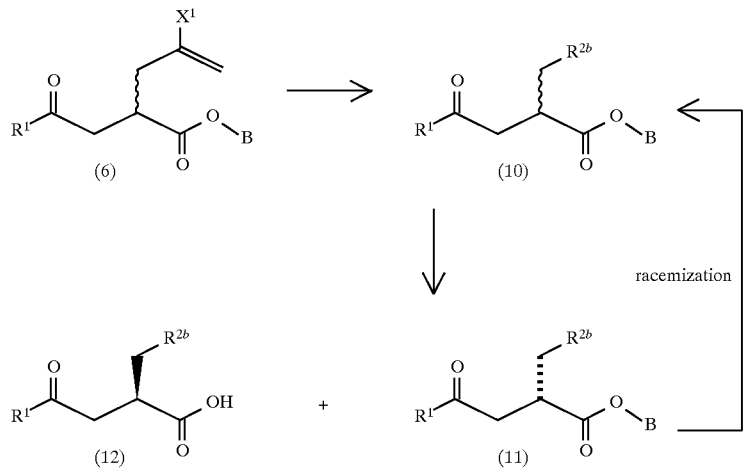

According to scheme 2, the succinyl derivative of formula 6 prepared as in scheme 1 is converted to the corresponding 2-aminothiazolyl derivative of formula 10 wherein $R^{2b}$ is 2-amino-4-thiazolyl, 2-(1,1-dimethylethyloxycarbonyl)amion-4-thiazolyl or 2-(amino protecting group)amino-4-thiazolyl according to the method of Hsaio et al. (Synthetic Comm. 1990, 20, 33507) and Morton et al. (Tetrahedron Letters 1993, 34, 4481). Briefly, the vinyl halide moiety of compound 6 is converted to an α-haloketone moiety by reacting the compound of formula 6 with N-bromosuccinimide or N-chlorosuccinimide or the like in a mixture of $H_2O$ and an inert solvent (for example, EtOAc/$H_2O$, acetonitrile/$H_2O$ and the like). Treatment of this latter α-haloketone derivative with thiourea gives the corresponding 2-aminothiazolyl derivative which can be further elaborated to 2-(amino protecting group)amino-4-thiazolyl by standard techniques. Treatment of the 2-aminothiazole derivative of formula 10 with an esterase (for example, Subtilisin Carlsberg or α-chymotrypsin) in either $H_2O$ or a mixture of $H_2O$ and a $H_2O$ miscible solvent (for example, acetone and the like) at a pH of about 7 to 8.5 gives a mixture of the (R)-acid of formula 12 and the (S)-ester of formula 11, which can be separated as described in scheme 1. The (S)-ester of formula 11 can be recycled by racemization under basic conditions to give the aminothiazole derivative of formula 10. By using procedures disclosed by Lavallée et al. (EP 589445, published Mar. 30, 1994), the (R)-acid of formula 12, which is a compound of formula II, prepared in this manner can be used directly in the preparation of renin inhibiting compounds of formula I and Ia.

Another general procedure for the preparation of compounds of formula II is outlined in scheme 3.

wherein $R^{1c}$ is selected from lower alkylamino, di(loweralkyl)amino or the monovalent radical A—$NR^3$ wherein A and $R^3$ are as defined herein, to give the racemic amide derivative of formula 22. The coupling of the carboxylic acid derivative of formula 20 and the amine derivative of formula 21 is effected by the classical dehydrative coupling of a free carboxyl of one reactant with the free amino group of the other reactant in the presence of coupling agent to form a linking amide bond. Description of such coupling agents are found in general textbooks on peptide chemistry; for example, M. Bodanszky, "Peptide Chemistry", 2nd rev ed, Springer-Verlag, Berlin, Germany, 1993. Examples of suitable coupling agents are N,N'-dicyclohexylcarbodiimide, 1-hydroxybenzotriazole in the presence of N,N'-dicyclohexylcarbodiimide, N-ethyl-N'-[(3-dimethylamino)propyl]-carbodiimide or the like. Treatment of the racemic amide derivative of formula 22 with an esterase as in scheme 1 or 2 results in a mixture of the (S)-acid of formula 24 and the (R)-ester of formula 23, which can be separated as described in scheme 1. The (R)-ester of formula 23 can be recycled by racemization under basic conditions to give the amide derivative of formula 22. By using procedures disclosed by Lavallée et al. (EP 589445, published Mar. 30, 1994), the (S)-acid of formula 24, which is a compound of formula II, prepared in this manner can be used directly in the preparation of renin inhibiting compounds of formula I and Ia.

Other starting materials for the preceding processes are known or can be readily prepared from known starting materials. The chemical reactions described above are generally disclosed in terms of their broadest application to the preparation of the compounds of this invention.

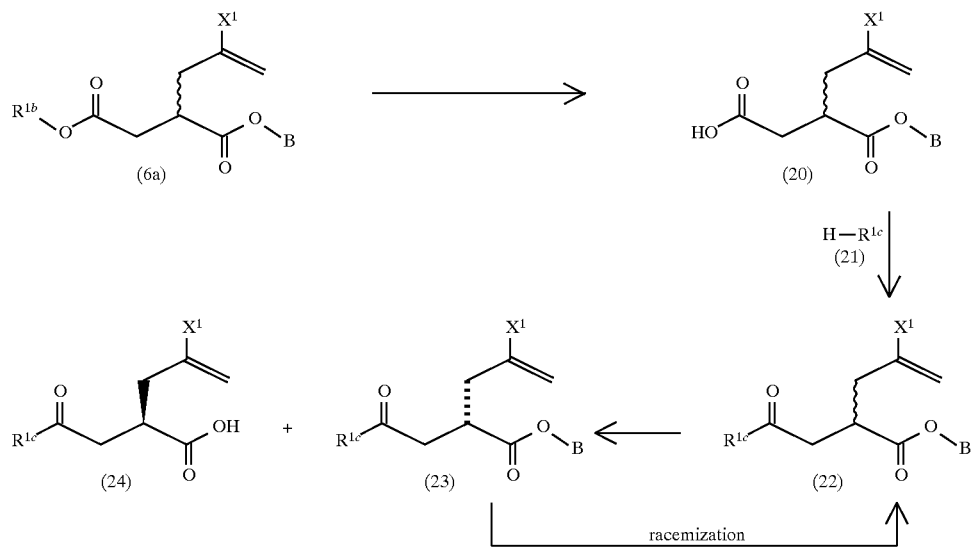

Scheme 3

The starting material in scheme 3 is the racemic compound 6a wherein $R^{1b}$ and B are lower alkyl, which is prepared according to scheme 1 (when $R^1$ of scheme 1 is lower alkoxy). The substituents $R^{1b}$ and B are selected such that $R^{1b}$ can be selectively removed from compound 6a. For example, when $R^{1b}$ is 1,1-dimethylethyl and B is methyl, acid hydrolysis of 6a (for example HCl, TFA and the like) will selectively remove $R^{1b}$ to give the free carboxylic acid derivative of formula 20. The free carboxylic acid derivative of formula 20 is coupled with the compound of formula 21

Occasionally, the reactions may not be applicable as described to each compound included within the disclosed scope. The compounds for which this occurs will be readily recognized by those skilled in the art. In all such cases, the reaction can be successfully performed by conventional modification known to those skilled in the art, e.g. by appropriate protection of interfering groups, by changing to alternative conventional reagents, by routine modification of reaction conditions, or by modification illustrated in the examples herein.

The following examples illustrate further this invention. Temperatures are given in degrees Celsius. Solution percentages or ratios express a volume to volume relationship, unless stated otherwise. Nuclear magnetic resonance spectra were recorded on a Bruker 200 or 400 MHz spectrometer; the chemical shifts ($\delta$) are reported in parts per million. The concentrations for the optical rotations are expressed in grams of the compound per 100 mL of solution. Enantiomeric purities were determined using chiral HPLC columns, and are indicated as Condition A: Chiralpak® AS 25 cm column, 0.25% ethanol in hexane, 0.5 mL/min, isocratic; or Condition B: Chiralcel® OD—H 15 cm+25 cm columns, 2% ethanol in hexane, 0.5 mL/min, isocratic. Abbreviations or symbols used in the examples include: DBU: 1,8-diazabicyclo[5.4.0]undec-7-ene; DCC: dicyclohexylcarbodiimide; DCU: dicyclohexylurea; DMF: dimethylformamide; EtOH: ethanol; EtOAc: ethyl acetate; $Et_2O$: diethyl ether; Hex: hexane; HOBt: 1-hydroxybenzotriazole; MeOH: methanol; NMM: N-methylmorpholine; THF: tetrahydrofuran.

EXAMPLE 1

2(S)-(2-Bromo-2-propenyl)-1,4-butenedioic Acid 4-(1,1-Dimethylethyl) Ester

EXAMPLE 1A 2-(2-Bromo-2-propenyl)-1,3-propanedioic Acid Dimethyl Ester

To a flask under nitrogen was added MeOH (67 mL), and sodium metal (1.15 g, 0.05 g atom) was added in portions over 30 min. To the resulting solution dimethyl malonate (13.2 g, 0.1 mol) in MeOH (10 mL) was added from a dropping funnel over 30 min. The solution was cooled to 0°, and 2,3-dibromopropene (12 g, 0.05 mol) in MeOH (15 mL) was added over 40 min. After a further 45 min at 0°, the pH of the mixture was neutral to litmus paper. The reaction medium was then concentrated under reduced pressure and the residue was dissolved in EtOAc (100 mL) and the resulting solution washed with distilled $H_2O$ (100 mL). The aqueous phase was re-extracted with $Et_2O$ (100 mL) and the combined organic phases were washed with brine, dried ($MgSO_4$), concentrated under reduced pressure and purified by distillation (82°–84°/1 Torr) to give the title compound as a colorless liquid (8.3 g, 66% yield): $^1$H NMR (400 MHz, $CDCl_3$) $\delta$5.69 (m, 1H, olefinic), 5.48 (d, J=1.9 Hz, 1H, olefinic), 3.81 (t, J=7.63 Hz, 1H), 3.75 (s, 6H), 3.02 (dd, J=0.95, 7.63 Hz, 2H); $13_C$NMR (100 MHz, $CDCl_3$) $\delta\delta$ 168.30, 129.18, 119.68, 52.59, 50.28, 40.36.

EXAMPLE 1B 2-(2-Bromo-2-propenyl)-2-(methoxycarbonyl)-1,4-butanedioic Acid 4-(1,1-Dimethylethyl) 1-Methyl Ester The title compound of Example 1A (0.5 g, 2 mmol) dissolved in THF (20 mL) was cooled to 0° under nitrogen. Potassium tert-butoxide (0.25 g, 2.2 mmol) was added all at once. After a further 20 min, tert-butyl bromoacetate (0.39 g, 2.2 mmol) was added dropwise from a syringe. The reaction mixture was stirred 16 h at room temperature. The excess base was destroyed by the addition of wet THF (2 ml) followed by the addition of $H_2O$ (40 mL) and EtOAc (40 mL). The organic phase was dried ($MgSO_4$) and concentrated under reduced pressure. The crude oil was purified by column chromatography ($SiO_2$) to give the title compound (0.619 g, 85% yield) as a colorless oil: $^1$H NMR (400 MHz, $CDCl_3$) $\delta$5.64 (broad s, 1H), 5.59 (broad s, 1H,), 3.75 (s, 6H), 3.35 (s, 2H), 3.07 (s, 2H), 1.43 (s, 9H); $13_C$ NMR (100 MHz, $CDCl_3$) $\delta$169.42, 168.43, 127.16, 122.35, 81.29, 54.64, 52.91, 43.53, 37.25, 27.92.

EXAMPLE 1C 2 (R,S)-(2-Bromo-2-propenyl)-1,4-butanedioic Acid 4-(1,1-Dimethylethyl) 1-Methyl Ester To a solution of LiBr (12.51 g, 0.144 mol) dissolved in $H_2O$ (5.2 mL) and DMF (20 mL) was added the title compound of Example 1B (52.6 g, 0.144 mol) in DMF (20 mL). This solution was heated to 135° for 6 h. The DMF was then removed under reduced pressure and the resulting residue diluted with $H_2O$ (60 mL), extracted twice with EtOAc (2×60 mL) and twice with $Et_2O$ (2×50 mL). The combined organic phases were washed with brine, dried ($MgSO_4$) and concentrated under reduced pressure to give a pale yellow oil (27.6 g, 62% yield). A sample of this material (9.55 g) was further purified by flash chromatography ($SiO_2$, eluent: 5% EtOAc/Hex) to give the title compound as a clear colorless oil (6.8 g), which was used in the following Examples 1D and 1E. HPLC analysis using a chiral column (Condition A: (R)-isomer, $t_R$ 9.2 min, (S)-isomer, $t_R$ 9.9 min) showed this sample to be a 1:1 ratio of the (R)- and (S)-enantiomers: $^1$H NMR (400 MHz, $CDCl_3$) $\delta$5.64 (s, 1H), 5.48 (d, J=1.6 Hz, 1H,), 3.71 (s, 3H), 3.14 (m, 1H), 2.85 (dd, J=6.4, 14.6 Hz, 1H), 2.61 (dd, J=8.3, 14.6 Hz, 1H), 2.57 (dd, J=8.6, 16.5 Hz, 1H), 2.48 (dd, J=5.4, 16.5 Hz, 1H), 1.44 (s, 9H); $^{13}$C NMR (100 MHz, $CDCl_3$) $\delta$173.90, 170.38, 130.46, 119.55, 80.91, 51.87, 42.75, 39.75, 35.82, 27.96.

EXAMPLE 1D

Kinetic Resolution of 2(R,S)-(2-Bromo-2-propenyl)-1,4-butanedioic Acid 4-(1,1-Dimethylethyl) 1-Methyl Ester Using $\alpha$-Chymotrypsin The purified title compound of Example 1C (0.513 g, 1.67 mmol) was dissolved in acetone (2 mL) and diluted with distilled $H_2O$ (5 mL). To this rapidly stirred solution was added $\alpha$-chymotrypsin (5 mg) (type I-S from Bovine Pancreas, crystallized 3×, obtained from the Sigma Chemical Co.). Aqueous NaOH (0.1N), added dropwise from a burette, was used to maintain the reaction at pH 8–9. The uptake of the NaOH solution was extremely slow (<2 drops of NaOH over 1 h) and after 1 h KCl salt (500 mg) was added as well as an extra 15 mg of the $\alpha$-chymotrypsin. In this specific reaction the pH was kept at 8–9 and after 4 days the reaction was not proceeding further (pH stable at pH 8). The reaction mixture was then diluted with distilled $H_2O$ (15 mL) and saturated aqueous $NaHCO_3$ solution (2 mL), extracted twice with methylene chloride (2×25 mL), dried ($MgSO_4$) and concentrated under reduced pressure to give the unreacted ester (300 mg), which was shown by HPLC using a chiral column (Condition A) to be a mixture of the (R)- and (S)-enantiomers in a ratio of 1.4:1.

The basic aqueous phase was rendered acidic (pH 5) by the addition of 10% (w/v) aqueous citric acid (~10 mL) and extracted three times with methylene chloride (3×30 mL). The methylene chloride phase was dried ($MgSO_4$) and concentrated under reduced pressure to give 2(S)-(2-bromo-2-propenyl)-1,4-butanedioic acid 4-(1,1-dimethylethyl) ester (66 mg, 28% yield). An aliquot of this material was reacted with diazomethane to give the corresponding methyl ester and analyzed by HPLC using a chiral column (Condition A) which indicated a ratio of 8.4:1 of (S)- to (R)-enantiomers (79% ee).

EXAMPLE 1E

Kinetic Resolution of 2(R,S)-(2-Bromo-2-propenyl)-1,4-butanedioic Acid 4-(1,1-Dimethylethyl) 1-Methyl Ester Using Subtilisin Carlsberg The title compound of Example 1C (5.01 g, 16.3 mmol) was dissolved in acetone (10 mL) and deionized $H_2O$ (30 mL). The system was equipped with an automatic pH titrator and a peristaltic pump connected to a 0.4M aqueous NaOH solution. The pH of the suspension was adjusted to 7.8. A crude preparation of Subtilisin Carlsberg (Alcalase® 2.4 L "food grade" enzyme preparation, Novo Nordisk Bioindustrials, USA), was added (0.2 g) and the automatic titrating system started with the pH set at 7.2. After 12 h at pH 7.2, the pH on the automatic titrator was reset to 7.5 and the reaction continued until the pH stabilized. The acetone was removed under reduced pressure and saturated aqueous $NaHCO_3$ (10 mL) was added to the aqueous phase. The aqueous phase was extracted twice with EtOAc (2×80 mL). The combined organic phases were dried ($MgSO_4$) and concentrated under reduced pressure to give the unreacted ester (2.67 g), which was shown by HPLC using a chiral column (Condition A) to be a mixture of the (R)- and (S)-enantiomers in a ratio of 68:1 (>97% ee). This material was saved and used for racemization and recycling (Example 1F).

The aqueous phase from the above extraction was rendered acidic by the addition of 10% aqueous HCl (20 mL) and then extracted twice with a 1:1 mixture of $EtOAc/Et_2O$ (2×80 mL). The latter extracts were washed with brine and dried ($MgSO_4$). The solvent was removed under reduced pressure and the residue dried under vacuo to give 2(S)-(2-bromo-2-propenyl)-1,4-butanedioic acid 4-(1,1-dimethylethyl) ester (2.246 g, 47% yield). An aliquot of this material was reacted with diazomethane to give the corresponding methyl ester and analyzed by HPLC using a chiral column (Condition A) which indicated a ratio of 214:1 of (S)- to (R)-enantiomers (>99% ee).

EXAMPLE 1F

Racemization of 2(R)-(2-Bromo-2-propenyl)-1,4-butanedioic Acid 4-(1,1-Dimethylethyl) 1-Methyl Ester To the unreacted ester of Example 1E (1.64 g, 5.34 mmol), which is a mixture of the (R)- and (S)-enantiomers in a ratio of 68:1, was added toluene (15 mL) and DBU (0.85 mL). This mixture was heated at reflux for 18 h and then diluted with $H_2O$ and extracted with EtOAc. The organic phase was washed serially with 5% aqueous HCl and brine, dried ($MgSO_4$) and concentrated under reduced pressure to yield material (1.57 g, 96% yield) identical to that obtained in Example 1C, which was shown by HPLC using a chiral column (Condition A) to be a mixture of the (R)-and (S)-enantiomers in a ratio of 1.1:1.

EXAMPLE 2

$N^4$-(Cyclohexylmethyl)-$N^4$-{2-{methyl{2-(2-pyridinyl)ethyl}-amino}-2-oxoethyl}-$N^1$-{1(S)-(cyclohexylmethyl)-2(R),3(S)-dihydroxy-5-methylhexyl}-2(R)-{(2-amino-4-thiazolyl) methyl}butanediamide

EXAMPLE 2A 2-(2-Chloro-2-propenyl)-1,3-propanedioic Acid Dimethyl Ester

A solution of dimethylmalonate (2381 g, 18.02 mol) in MeOH (500 mL) was added to a stirred solution of 25% (w/w) NaOMe in MeOH (1071 g, 4.95 mol) and MeOH (500 mL). The mixture was heated to an internal temperature of 70°. 2,3-Dichloropropene (511 g, 4.60 mol) in MeOH (500 mL) was added dropwise over 12 h. Thereafter the mixture was stirred at 70° for 8 h. The MeOH was removed under reduced pressure. The residue was partitioned between $Et_2O$ (2 L) and $H_2O$ (2 L). The organic phase was separated and the aqueous phase was extracted with two additional portions of $Et_2O$ (2×1 L). The combined organic phases were washed serially with 1N aqueous HCl (500 mL), $H_2O$ (2×1 L) and brine (2×500 mL), dried ($MgSO_4$) and concentrated under reduced pressure to give a dark orange oil consisting of unreacted malonate, the desired monoalkylated product and some corresponding dialkylated material. Most of the unreacted dimethyl malonate was removed by rotary evaporation under high vacuum (1 Torr) with a bath temperature of 70°. Dimethylmalonate (1381 g) contaminated with 6% of monoalkylated product (by $^1H$ NMR) was recovered and recycled in future runs.

The residual material (800 g) was fractionally distilled under vacuum to give a number of fractions as indicated in the following table:

| Bp° C./Torr | Weight | % Malonate | % Mono-alkylated | % Di-alkylated |
| --- | --- | --- | --- | --- |
| 80–90/2 | 25 g | 37 | 63 | 0 |
| 90–100/2 | 39 g | 16 | 84 | 0 |
| 100/2 | 651 g | 1 | 97.5 | 1.5 |
| 105–110/.25 | 44 g | 0 | 12.5 | 87 |

The yield of the title compound was 651 g (97% pure by HPLC; 68% yield based on 2,3-dichloropropene): $^1H$ NMR (400 MHz, $CDCl_3$) δ5.24 (m, 2H), 3.81 (t, J=7.6 Hz, 1H), 3.76 (s, 6H), 2.95 (m, 2H); IR (neat) ν1740, 1635 $cm^{-1}$.

EXAMPLE 2B 2-(2-Chloro-2-propenyl)-2-(methoxycarbonyl)-1,4-butanedioic Acid 4-(1,1-Dimethylethyl) 1-Methyl Ester A mixture of the title compound of Example 2A (519.6 g, 2.564 mol) and tert-butyl bromoacetate (500 g, 2.564 mol) was added dropwise over 30 min to a stirred mixture of 10N aqueous NaOH (2.56 L, 25.6 mol) and benzyltriethylammonium chloride (2.56 g, 11.2 mmol) at 10°. The reaction mixture was stirred at room temperature for 2 h and then diluted with Hex (750 mL). The organic phase was separated and washed serially with $H_2O$ (100 mL) and brine (2×100 mL), dried ($MgSO_4$), and concentrated under reduced pressure to give the title compound (822 g, 100% yield) which was used without further purification for the next step (Example 2C). $^1H$ NMR (400 MHz, $CDCl_3$) δ5.32 (d, J=1.4 Hz, 1H), 5.20 (broad s, 1H), 3.75 (s, 6H), 3.25 (broad s, 2H), 3.06 (s, 2H), 1.43 (s, 9H). MS (FAB) m/z 321 ($MH^+$).

EXAMPLE 2C

2(R,S)-(2-Chloro-2-propenyl)-1,4-butanedioic Acid 4-(1,1-Dimethylethyl) 1-Methyl Ester The title compound of Example 2B (1502 g, 4.18 mol) was dissolved in MeOH (2650 mL). While maintaining a temperature of 30° or below for the ensuing mixture, a cold solution of KOH (329 g, 5.85 mol) in $H_2O$ (1335 mL) was added dropwise over 20 min. The mixture was stirred vigorously for 24 h.

Thereafter, the MeOH was evaporated under reduced pressure. The resulting aqueous phase was extracted first with Hex (3×750 mL), rendered acidic (pH 1) by the addition of concentrated HCl (~500 mL) and then extracted with toluene (3×1 L). The latter extract was dried (MgSO$_4$) and then heated at reflux for 24 h to effect decarboxylation. At the completion of this period, the reaction mixture was concentrated under reduced pressure. The residue was distilled under reduced pressure (128°–132°/0.75 Torr) to give the title racemic compound (867 g, 79% yield) as a colorless liquid: $^1$H NMR (400 MHz, CDCl$_3$) δ5.25 (d, J=1.3 Hz, 1H), 5.20 (broad s, 1H), 3.71 (s, 3H), 3.14 (m, 1H), 2.76 (ddd, J=14.3, 6.4, 1.0 Hz, 1H), 2.59 (dd, J=16.5, 8.3 Hz, 1H), 2.53 (dd, J=14.9, 8.4 Hz, 1H), 2.48 (dd, J=16.5, 5.1 Hz, 1H), 1.44 (S, 9H) ; $^{13}$C NMR (100 MHz, CDCl$_3$) δ173.9, 170.4, 139.1, 114.9, 80.8, 51.8, 40.6, 39.1, 35.9, 27.9. MS (FAB) m/z 263 (MH$^+$).

EXAMPLE 2D

Kinetic Resolution of 2 (R,S)-(2-Chloro-2-propenyl)-1,4-butanedioic Acid 4-(1,1-Dimethylethyl)1-Methyl Ester Using Subtilisin Carlsberg The title compound of Example 2C (860.00 g, 3.273 mol) was placed in a 5 L flask and suspended in acetone (15 mL) and deionized H$_2$O (1.5 L). The system was equipped with an automatic pH titrator and a peristaltic pump connected to a 3N aqueous NaOH solution (550 mL, ±0.5 equivalents). The pH of the suspension was adjusted to 7.5. A crude preparation of Subtilisin Carlsberg (Alcalase® 2.4 L "food grade" enzyme preparation, Novo Nordisk Bioindustrials, USA) was added (10 g) and the automatic titrating system started with the pH set at 7.5. After 22 h at pH 7.5, the pH on the automatic titrator was then set to 8.0 and the reaction continued for another 96 h. The unreacted (R)-ester was extracted with EtOAc (3×700 mL), washed serially with H$_2$O and brine, dried (MgSO$_4$) and concentrated under reduced pressure to give a colorless oil (442 g), which was shown by HPLC using a chiral column (Condition A) to be a mixture of the (R)-and (S)-enantiomers in a ratio of 21:1. This material was saved for racemization and recycling.

The aqueous phase from the above extraction was rendered acidic (pH 1) by the addition of 6N aqueous HCl (~800 mL) and then extracted with EtOAc (3×1 L). The latter extracts were washed serially with H$_2$O and brine and then dried (MgSO$_4$). The solvent was removed under reduced pressure and the residue was dried under vacuo to give 2(S)-(2-chloro-2-propenyl)-1,4-butanedioic acid 4-(1, 1-dimethylethyl) ester (390 g, 96% of theoretical amount) which was >96% homogeneous by HPLC. An aliquot of this material was reacted with diazomethane to give the corresponding methyl ester and analyzed by HPLC using a chiral column (Condition A) which indicated a ratio of 109:1 of (S)-to (R)-enantiomers (99% ee) : [α]$_D^{25}$ −4.58° (c 1, MeOH), [α]$_{Hg436}^{25}$ −6.11° (c 1, MeOH); $^1$H NMR (400 MHz, CDCl$_3$) δ11.5 (broad S, 1H), 5.27 (d, J=1.3 Hz, 1H), 5.22 (broad s, 1H), 3.16 (m, 1H), 2.81 (dd, J=14.3, 6.0 Hz, 1H), 2.63–2.49 (m, 3H), 1.47 (s, 9H); $^{13}$C NMR (100 MHz, CDCl$_3$) δ179.9, 170.4, 138.9, 115.3, 81.2, 40.2, 39.1, 35.5, 27.9; MS (FAB) m/z 249 (MH$^+$). This crude material is of sufficient purity to be used in the coupling reactions of Examples 2E and 2F without further purification.

EXAMPLE 2E

Alternative Kinetic Resolution of 2(R,S)-(2-Chloro-2-propenyl)-1,4-butanedioic Acid 4-(1,1-Dimethylethyl) 1-Methyl Ester Using Subtilisin Carlsberg In this example, the enzymatic hydrolysis of the title compound of Example 2C is carried out without acetone as a co-solvent.

The title compound of Example 2C (0.505 g, 1.92 mmol) was suspended in H$_2$O (6 mL) and rapidly stirred. The system was equipped with an automatic pH titrator and a peristaltic pump connected to a 0.1N aqueous NaOH solution. The pH of the biphasic solution was adjusted to 7.6 and a crude preparation of Subtilisin Carlsberg (Alcalase® 2.4 L "food grade" enzyme preparation, Novo Nordisk Bioindustrials, USA) was added (0.112 g) and the automatic titrating system started with the pH set at 7.5. After 3 h, the reaction mixture was diluted with 5 mL saturated aqueous NaHCO$_3$, EtOAc (40 mL) and H$_2$O (20 mL). The organic phase was separated, dried (MgSO$_4$) and concentrated under reduced pressure to give the unreacted (R)-ester (0.25 g, 50% yield). Analysis by HPLC using a chiral column (Condition A) showed that the optical purity of the (R)-enantiomer was >98% ee.

The aqueous phase from the above extraction was rendered acidic (pH 3) by the addition of 5% aqueous HCl, and extracted with EtOAc (50 mL). The organic phase was dried (MgSO$_4$) and concentrated under reduced pressure to give 2(S)-(2-chloro-2-propenyl)-1,4-butanedioic acid 4-(1,1-dimethylethyl) ester (0.215 g, 45% yield). An aliquot of this material was reacted with diazomethane to give the corresponding methyl ester and analyzed by HPLC using a chiral column (Condition A). The optical purity of the (S)-enantiomer was 97.5% ee.

EXAMPLE 2F

4-{{1(S)-(Cyclohexylmethyl)-2(R),3(S)-dihydroxy-5-ethylhexyl}amino}-3(S)-2-chloro-2-propenyl)-4-oxobutanoic Acid (1,1-Dimethylethyl) Ester The title compound of Example 2D (41.69 g, 167.6 mmol), 2(S)-2-amino-1-cyclohexyl-6-methyl-3(R),4(S)-heptanediol (40.00 g, 164.4 mmol) (J. R. Luly et al., J. Org. Chem. 1988, 53, 6109), HOBt (25.92 g, 169.3 mmol) and N-methylmorpholine (16.29 g, 161.1 mmol) were dissolved in THF (450 mL) and the solution cooled in an ice-water bath. DCC (34.59 g, 167.6 mmol) in THF (50 mL) was added and the mixture stirred 30 min at 5° and then for a further 17 h at room temperature. The precipitated solid was removed by filtration and the filtrate concentrated under reduced pressure. The residue was dissolved in EtOAc (1 L), the suspension filtered to remove precipitated DCU and the filtrate washed serially with 1N aqueous HCl (3×300 mL), H$_2$O (250 mL), 3N aqueous NaOH (3×300 mL) and brine. After drying (MgSO$_4$), the solvent was removed under reduced pressure to give a white solid. Recrystallisation from EtOAc/Hex gave the title compound (99.3% homogeneity by HPLC) as a white solid (77.91 g, 71% yield): mp 144°–1460°; [α]$_D^{25}$ −41.39° (c 1, MeOH); $^1$H NMR (400 MHz, CDCl$_3$) δ5.91 (broad d, J=8.6 Hz, 1H), 5.27 (m, 2H), 4.29 (dt, J=9.0, 4.7 Hz, 1H), 4.19 (m, 1H), 3.21 (m, 2H), 3.04 (m, 1H), 2.73 (dd, J=14.0, 8.9 Hz, 1H), 2.63 (dd, J=17.2, 9.4 Hz, 1H), 2.43 (dd, J=14.3, 6.0 Hz, 1H), 2.38 (dd, J=17.1, 4.2 Hz, 1H), 1.89 (m, 1H), 1.8–1.1 (m, 15H), 1.46 (s, 9H), 1.0–0.77 (m, 2H), 0.94 (d, J=6.7 Hz, 3H), 0.87 (d, J=6.4 Hz, 3H); $^{13}$C NMR (100 MHz, CDCl$_3$) δ175.0, 171.4, 139.4, 115.6, 81.5, 77.7, 69.8, 47.5, 42.8, 41.7, 40.8, 39.7, 37.2, 34.1, 33.9, 32.8, 28.3, 26.6, 26.3, 26.2, 24.8, 24.1, 22.0. MS (FAB) m/z 474 (MH$^+$). Anal. Calcd. for C$_{25}$H$_{44}$ClNO$_5$: C, 63.34; H, 9.35; N, 2.95. Found: C, 63.50; H, 9,62; N, 3.00.

EXAMPLE 2G

4-{{1(S)-(Cyclohexylmethyl)-2(R),3(S)-dihydroxy-5-methylhexyl}amino}-3(S)-(2-chloro-2-propenyl)-4-oxo-butanoic Acid The title compound of Example 2F (34.20 g, 72.1 mmol) was added to TFA (100 mL) and the mixture stirred 24 h at room temperature. The volatiles were removed under reduced pressure and the residue coevaporated twice with MeOH (100 mL). The residue was dissolved in MeOH (100 mL) and 3N aqueous NaOH (100 mL) was added. The mixture was stirred 4 h at room temperature. The MeOH was removed under reduced pressure and the residue rendered acidic (pH 1) with concentrated HCl. The precipitated product was collected by filtration, washed with $H_2O$ and dried to give the title compound (29.36 g, 97% yield): mp 193°–196°; $[\alpha]_D^{25}$ −49.2° (c 1, MeOH); $^1$H NMR (400 MHz, DMSO-$d_6$) δ7.83 (d, J=8.7 Hz, 1H), 5.34 (s, 1H), 5.20 (s, 1H), 4.61 (broad d, J=5.7 Hz, 1H),4.48 (broad s, 1H), 4.09 (m, 1H), 3.07 (t, J=7.2 Hz, 2H), 2.90 (broad m, 1H), 2.65 (dd, J=14.7, 7.6 Hz, 1H), 2.48 (dd, J=15.4, 7.0 Hz, 1H), 2.42 (dd, J=14.7, 6.6 Hz, 1H), 2.28 (dd, J=16.6, 5.8 Hz, 1H), 1.77 (m, 1H), 1.7–1.5 (m, 6H), 1.45 (m, 1H), 1.38–1.03 (m, 6H), 0.96–0.7 (m, 2H), 0.87 (d, J=6.6 Hz, 3H), 0.70 (d, J=6.6 Hz, 3H); MS (FAB) m/z 418 (MH$^+$). Anal. Calcd. for $C_{21}H_{36}ClNO_5$: C, 60.35; H, 8.68; N, 3.35. Found: C, 60.15; H, 8.79; N, 3.40.

EXAMPLE 2H $N^4$-(Cyclohexylmethyl)-$N^4$-{2-{methyl{2-(2-pyridinyl)-ethyl}amino}-2-oxoethyl}-$N^1$-{1(S)-(cyclohexylmethyl)-2(R),3(S)-dihydroxy-5-methylhexyl}-2(R)-(2-chloro-2-propenyl) butanediamide The title compound of Example 2G (10.00 g, 23.92 mmol) and N-methylmorpholine (5.8 mL, 52.6 mmol) were suspended in cold (5°) THF (75 mL) and the mixture stirred until all solids were dissolved. Pivaloyl chloride (2.94 mL, 23.92 mmol) was added and the mixture stirred 10 min in an ice-water bath. N-{2-(2-pyridinyl)ethyl}-N-methyl-2-{(cyclohexylmethyl)amino}acetamide (8.00 g, 27.5 mmol) (Lavallée et al, EP 589445, published Mar. 30, 1994) in THF (15 mL) was added and the cooling bath removed. The mixture was stirred at room temperature for 2 h. The reaction was quenched with $H_2O$ (50 mL) and the THF removed under reduced pressure. The residue was extracted with EtOAc and the organic phase washed serially with 1N aqueous NaOH and $H_2O$, dried (MgSO$_4$), concentrated under reduced pressure and the residue crystallized twice from hot EtOAc/Hex. The title compound was obtained as a white solid (12.25 g, 74% yield, >97% homogeneity by RP-HPLC): Rf 0.49 (9:1 CHCl$_3$/MeOH); mp 139.5°–140.5°; $[\alpha]_D^{23}$ −32.3° (c 1, MeOH); $^1$H NMR (400 MHz, CDCl$_3$) exists as a mixture of rotamers: δ8.60, 8.57 and 8.52 (broad d, J=4.8 Hz, total 1H), 7.62 (m, 1H), 7.25 (m, 1H), 7.16 (m, 1H), 6.78, 6.62 and 6.57 (d, J=8.3 Hz, total 1H), 5.26 (m, 2H), 4.33 (m, 2H), 4.11 (m, 1H), 4.05–3.6 (m, 3H), 3.3–2.8 (m, 9H), 2.94 (s, 3H), 2.69–2.4 (m, 3H), 1.90 (m, 1H), 1.8–1.1 (m, 25H), 1–0.8 (m, 10H); MS (FAB) m/z 689 (MH$^+$). Anal. Calcd. for $C_{38}H_{61}ClN_4O_5$: C, 66.21; H, 8.92; N, 8.13. Found: C, 66.07; H, 9.06; N, 8.10.

EXAMPLE 2I $N^4$-(Cyclohexylmethyl)-$N^4$-{2-(methyl{2-(2-pyridinyl)ethyl{amino}-2-oxoethyl}-$N^1$1(S)-(cyclohexylmethyl)-2(R),3(S)-dihydroxy-5-methylhexyl}-2(R)-{(2-amino-4-thiazolyl) methyl}butanediamide The title compound of Example 2H (1.069 g, 1.55 mmol) was dissolved in dichloromethane (30 mL), and para-toluenesulfonic acid monohydrate (0.019 g, 0.1 mmol) was added followed by 2-methoxypropene (0.745 mL, 7.75 mmol). The mixture was stirred for 60 h at room temperature. Volatiles were removed under reduced pressure and the residue dissolved in a mixture of 2:1 EtOAc:$H_2O$ (60 mL). After cooling in an ice-water bath, N-bromosuccinimide (0.32 g, 1.8 mmol) was added and the mixture stirred 3 h at 5° and 3 h at room temperature. Thiourea (0.142 g, 1.86 mmol) was added and the reaction mixture immersed in a preheated oil bath at 70°. After 1 h, the reaction was judged complete by RP-HPLC. The suspension was rendered basic (pH 11) by the addition of 3N aqueous NaOH and extracted with EtOAc. The organic phase was washed serially with 1N aqueous NaOH and $H_2O$, dried (MgSO$_4$), and concentrated under reduced pressure. The residue was dissolved in a small amount of EtOAc and the product precipitated by the addition of Hex. The cream colored precipitate was collected, washed with Hex and dried under reduced pressure (0.95 g, 84% yield, 96% homogeneity by RP-HPLC). An analytical sample was obtained by a second precipitation from EtOAc/hexane to give a 97% homogeneous preparation of the title compound identical in all respect to material previously prepared by the chiral auxiliary route (Lavallée et al, EP 589445): R$_f$ 0.21 (9:1 CHCl$_3$/MeOH); mp 84°–90° (not well defined); precipitated sample from MeOH/$H_2O$: $[\alpha]_D^{25}$−21.6° (c 1 MeOH); 1H NMR (400 MHz, DMSO-$d_6$) exists as a mixture of rotamers: δ8.3 (m, 1H), 7.69 (m, 1H), 7.52 (m, 1H), 7.3–7.18 (m, 2H), 6.73 (broad s, 1H), 6.69 (s, 1H), 6.16, 6.15, 6.09 and 6.04 (s, total 1H), 4.62 (m, 1H), 4.5 (m, 1H), 4.2–4.0 (m, 2H), 3.85 (t, J=17.4 Hz, 0.7H), 3.7–3.5 (m, 2.3H), 3.1–2.6 (m, 11H), 2.5–2.0 (m, 2.7H), 1.8–1.0 (m, 24H), 0.9–0.7 (m, 4H), 0.86 (d, J=6.6 Hz, 3H), 0.78 (d, J=6.3 Hz, 3H); MS (FAB) m/z 727 (MH$^+$). Anal. Calcd. for $C_{39}H_{62}N_6O_5S$: C, 64.43; H, 8.60; N, 11.56. Found: C, 64.04; H, 8.76; N, 11.35.

EXAMPLE 3

4-{(Cyclohexylmethyl)-{2-{methyl{2-(2-pyridinylethyl}amino}-2-oxoethyl}amino}-2(S)-(2-chloro-2-propenyl)-4-oxobutanoic Acid

EXAMPLE 3A

2(R,S)-(2-Chloro-2-propenyl)-1,4-butanedioic Acid 1-Methyl Ester

The title compound of Example 2C (607.76 g, 2.31 mol) was added to an ice-cold solution of aqueous 4N HCl in dioxane (1600 mL). The mixture was allowed to warm up to room temperature and stirred for 40 h. Volatiles were removed under vacuo to give a yellow oil which was dissolved in ether (250 mL). Hex was added until the solution became cloudy (~650 mL). After seeding, the product crystallized at room temperature. After cooling overnight to 5°, the product was collected, washed with 10% ether in Hex, then with Hex. After drying in vacuo, the title compound was obtained as a white crystalline solid (407.4 g, 85% yield): mp 61°–64°; $^1$H NMR (400 MHz, CDCl$_3$) δ11.5 (broad s, 1H), 5.27 (d, J=1.3 Hz, 1 H), 5.22 (broad s, 1H), 3.72 (s, 3H), 3.24–3.16 (m, 1H), 2.84–2.71 (m, 2H), 2.65–2.54 (m, 2H); $^{13}$C NMR (100 MHz, CDCl$_3$) δ177.3, 173.7, 138.6, 115.2, 52.0, 40.3, 38.5, 33.9; MS (FAB) m/z 207 (MH$^+$). Anal. Calcd. for $C_8H_{11}ClO_4$: C, 46.50; H, 5.37. Found: C, 46.12; H, 5.35.

EXAMPLE 3B

4-{(Cyclohexylmethyl)-{2-{methyl{2-(2-pyridinyl) ethyl}amino}-2-oxoethyl}amino}-2(R,S)-(2-chloro-2-propenyl)-4-oxobutanoic Acid 1-Methyl Ester The title compound of Example 3A (20.00 g, 96.8 mmol), N-{2-(2-pyridinyl)ethyl}-N-methyl-2-{(cyclohexylmethyl)

amino}acetamide (26.68 g, 92.2 mmol) (Lavallée et al., EP 589445, published Mar. 30, 1994), HOBt (15.00 g, 98.0 mmol) and NMM (17.00 g, 168 mmol) were suspended in THF (150 mL) and the mixture stirred at room temperature until all solids dissolved. DCC (20.00 g, 97 mmol) in THF (10 mL) was added and the mixture stirred overnight at room temperature. Volatiles were removed under reduced pressure and the residue dissolved in EtOAc. The solution was filtered to remove insoluble DCU, then washed serially with water (2×), 3N NaOH (3×), water (2×) and brine (2×). After drying over anhydrous sodium sulfate, volatiles were removed under reduced pressure to give an oily orange residue which was dried in vacuo to yield the title compound (42.28 g, 96% yield, crude product): $^1$H NMR (400 MHz, $CDCl_3$; exists as a mixture of rotamers): δ8.60–8.50 (m, 1H), 7.60 (m, 1H), 7.20–7.10 (m, 2H), 5.30–5.15 (m, 2H), 4.20–3.70 (m, 4H), 3.70 and 3.68 (two s, 3H), 3.30–2.20 (m, 10H), 2.90 (s, 3H), 1.80–1.40 (m, 4H), 1.25–1.10 (m, 2H), 0.98–0.80 (m, 2H).

EXAMPLE 3C

4-{(Cyclohexylmethyl)-{2-{methyl{2-(2-pyridinyl)-ethyl}amino}-2-oxoethyl}amino}-2(S)-(2-chloro-2-propenyl)-4-oxobutanoic Acid The title compound of Example 3B (196.2 g, 0.41 mole), was dissolved in warm acetone (150 mL) and diluted with $H_2O$ (350 mL). The solution was adjusted to pH 7 by the addition of aqueous $KHSO_4$ and a crude preparation of Subtilisin Carlsberg (Alcalase® 2.4 L "food grade" enzyme preparation, Novo Nordisk Bioindustrials, USA) (5 g) was added. The solution was stirred vigorously and the pH of the solution was maintained between 7 and 8 using a pH titrator and a peristaltic pump connected to a 1N aqueous NaOH solution and the reaction was continued until the pH stabilized. The reaction mixture was concentrated under reduced pressure and extracted with EtOAc (4×200 mL). The combined organic phase was washed serially with $H_2O$ (2×100 mL) and brine (100 mL), dried ($MgSO_4$), concentrated under reduced pressure and the residue partially purified by passage through a 3 cm pad of silica gel using EtOAc (1 L) as the eluent. Removal of the solvent gave the (R)-ester as a dark brown oil (103.69 g, 52% yield), which was saved for racemization and recyling (described in Example 3D). HPLC analysis was performed on an aliquot of this material using a chiral column (Condition B: (R)-isomer, $t_R$ 154.1 min (98.8%); (S)-isomer, $t_R$ 170.8 min (1.2%)): $^1$H NMR (methyl ester, mixture of rotamers; 400 MHz, $CDCl_3$) δ8.63–8.50 (m, 1H), 7.67–7.57 (m, 1H), 7.24–7.10 (m, 2H), 5.27–5.15 (m, 2H), 4.23–3.67 (m, 6H), 3.31–2.2 (m, 9H), 1.8–1.1 (m, 9H), 1.0–0.8 (m, 2H); MS(FAB) m/z 478 (MH$^+$).

The aqueous phase from the above extraction was rendered acidic (pH 4) with 20% aqueous $KHSO_4$ and extracted with EtOAc (4×200 mL). The combined organic phase was filtered to remove some insoluble particles, washed serially with $H_2O$ (200 mL) and brine (2×200 mL), dried ($MgSO_4$), and concentrated under reduced pressure to give the title compound as a yellow-brown foam (67.35 g, 34.3% yield): $^1$H NMR (mixture of rotamers; 400 MHz, $CDCl_3$) δ12–11 (broad s, 1H), 8.63–8.5 (m, 1H), 7.70–7.63 (m, 1H), 7.30–7.14 (m, 2H), 5.32–5.18 (m, 2H), 4.08 and 4.0 (AB quartets, major rotamers, 2H), 3.80–3.61 (m, 2H), 3.25–2.5 (m, 12H), 1.8–1.4 (m, 6H), 1.25–1.10 (m, 3H), 0.98–0.80 (m, 2H); MS(FAB) m/z 464 (MH$^+$).

The enantiomeric purity of the (S)-acid was determined by HPLC using a chiral column (Condition B: (R)-isomer, $t^R$ 157.4 min (3%); (S)-isomer, $t_R$ 166.8 min (97%)) after conversion of an aliquot to the methyl ester using diazomethane in $Et_2O$: $^1$H NMR (methyl ester, mixture of rotamers; 400 MHz, $CDCl_3$) δ8–8.50 (m, 1H), 7.67–7.57 (m, 1H), 7.24–7.10 (m, 2H), 5.27–5.15 (m, 2H), 4.23–3.67 (m, 6H), 3.31–2.2 (m, 9H), 1.8–1.1 (m, 9H), 1.0–0.8 (m, 2H).

EXAMPLE 3D

Racemization of 4-{(Cyclohexylmethyl)-{2-{methyl{2-(2-pyridinyl)ethyl}-amino}-2-oxoethyl}amino}-2(R,S)-(2-chloro-2-propenyl)-4-oxobutanoic Acid 1-Methyl Ester The unreacted (R)-ester obtained from the first extraction in Example 3C was racemized for recycling as follows. The (R)-ester (3.19 g, 6.67 mmol) was dissolved in MeOH (10 mL) and a 25% (w/w) solution of NaOMe in MeOH (152 μL, 0.66 mmol) was added. The reaction mixture was stirred 17 h at 60°. HPLC analysis using a chiral column (Condition B: (R)-isomer, $t_R$ 163.2 min (50%); (S)-isomer, $t_R$ 176.6 min (50%)) indicated complete racemization.

EXAMPLE 4

2(S)-(2-Bromo-2-propenyl)-1,4-butanedioic Acid 4-(1,1-Dimethylethyl) Ester

The title compound can be prepared following the procedures described in Example 1 with the following modifications: NaOMe/MeOH was replaced with NaHMDS (1M in THF), and dimethyl malonate was replaced with diethyl malonate.

Alternatively, the title compound was also prepared in the following manner. The title compound of Example 1C (3.0 g, 9.77 mmol) was dissolved in THF (12 mL) and $H_2O$ (4 mL) before being treated with LiOH (0.82 g, 19.5 mmol). The mixture was rapidly stirred for 15 h before being diluted with EtOAc (100 mL) and saturated aqueous $NaHCO_3$ (30 mL). The phases were separated and the aqueous phase rendered acidic by the addition of 6N aqueous HCl. The aqueous phase was then extracted with EtOAc (2×80 mL). The combined organic phases were washed with saturated brine (1×60 mL) and dried ($MgSO_4$). Concentration under reduced pressure gave the carboxylic acid as a colourless oil which solidified upon standing (2.34 g, 82% yield): $^1$H NMR (200 MHz, $CDCl_3$) δ5.7 (broad d, 1H), 5.55 (dd, 1H), 3.2 (m, 1H), 2.9 (m, 1H); MS (FAB) m/z 293, 295 (M+). Exact mass; calc. 293.0403, found 293.0388.

The carboxylic acid (1.09 g, 3.72 mmol) from above was dissolved in acetonitrile (15 mL) and cooled to 0°. DBU (0.63 mL, 4.09 mmol) was then added and incubated for 10 min after which iodoethane (0.36 mL, 4.46 mmol) was added. The reaction was allowed to stir for 16 h before being concentrated. The residue was dissolved in EtOAc (80 mL) and washed serially with saturated aqueous $NaHCO_3$ (1×50 mL), 5% aqueous HCl (1×40 mL), and saturated brine (1×50 mL). The organic phase was dried ($MgSO_4$) and concentrated under reduced pressure. Purification by silica chromatography with 10% EtOAc/Hex gave 0.45 g (40% yield) of racemic 2(R,S)-(2-bromo-2-propenyl)-1,4-butanedioic acid 4-(1,1-dimethylethyl) 1-ethyl ester: MS (FAB) m/z 322.8 (M$^+$). Anal. Calcd. for $C_{13}H_{21}O_4Br$: C, 48.61; H, 6.59. Found: C, 48.75; H, 6.68.

The racemic compound from above was submitted to a kinetic resolution using Subtilisin Carlsberg following the procedure of Example 2E. The title compound was obtained with 75% ee (analysis performed by HPLC using a chiral column (Condition A) after derivatization of an aliquot with diazomethane to the corresponding methyl ester) and 39.5% yield.

EXAMPLE 5

2(R)-[(2-Amino-4-thiazolyl)methyl]-1,4-butanedioic Acid 4-(1,1-Dimethylethyl) Ester The title compound from Example 2C (5.0 g, 16.3 mmol) was dissolved in acetonitrile (20 mL) and deionized water (7 mL). N-bromosuccinimide (4.06 g, 23 mmol) was added in one portion. The mixture was stirred for 35 min before the excess N-bromosuccinimide was quenched with 2-methoxypropene (0.63 mL, 6.5 mmol). After 3 min the reaction mixture was treated with thiourea (1.5 g, 19.6 mmol) in one portion. The reaction was stirred for 1 h before being concentrated under reduced pressure. The residue was dissolved in EtOAc (150 mL) and washed serially with water (100 mL) and saturated aqueous $NaHCO_3$ (30 mL). The organic phase was dried ($MgSO_4$) and concentrated under reduced pressure. The crude extract was purified by flash silica chromatography (5% $MeOH/CHCl_3$) to give 2.0 g (41% yield) of racemic 2(R,S)-[(2-amino-4-thiazolyl)methyl]-1,4-butanedioic acid 4-(1,1-dimethylethyl) 1-methyl ester: $^1H$ NMR (400 MHz, $CDCl_3$1 8 6.17 (s, 1H), 4.89 (bs, 2H), 3.68 (s, 3H), 3.2 (m, 1H), 2.95 (m, 1H), 2.55–2.8 (m, 2H), 2.45 (m, 1H), 1.43 (s, 9H); MS (FAB) m/z 301.4 $(MH)^+$; HRMS (FAB) Calcd. for $(MH)^+$, 301.12219. Found 301.12320.

The racemic compound from above was submitted to a kinetic resolution using Subtilisin Carlsberg following the procedure of Example 2E. The title compound was obtained with 97% ee (analysis performed by HPLC using a chiral column (Condition A) after derivatization of an aliquot with diazomethane to the corresponding methyl ester) and 26.5% yield.

EXAMPLE 6

2(R)-{(2-(1,1-dimethylethoxycarbonyl)amino-4-thiazolyl)methyl}-1,4-butanedioic Acid 4-(1,1-Dimethylethyl) Ester The amino group of the racemic 2(R,S)-{(2-amino-4-thiazolyl)methyl}-1,4-butanedioic acid 4-(1,1-dimethylethyl) 1-methyl ester from Example 5 was protected as a t-butyl carbamate group using $(Boc)_2O$ and a suitable base in THF. Purification by silica chromatography gave the desired racemic 2(R,S)-{(2-(1,1-dimethylethyloxycarbonyl)amino-4-thiazolyl)-methyl}-1,4-butanedioic acid 4-(1,1-dimethylethyl) 1-methyl ester: $^1$ H NMR (400MHz, $CDCl_3$) δ8.85 (bs, 1H), 6.55 (s, 1H), 3.66 (s, 3H), 3.17 (m, 1H), 3.05 (m, 1H), 2.84 (m, 1H), 2.57 (m, 1H), 2.41 (m, 1H), 1.6 (s, 9H), 1.4 (s, 9H); MS (FAB) m/z 401.1 $(MH)^+$; HRMS (FAB) Calcd. for $(MH)^+$, 401.17462. Found 401.17570.

The racemic compound from above was submitted to a kinetic resolution using Subtilisin Carlsberg following the procedure of Example 2E. The title compound was obtained with 82.5% ee (analysis performed by HPLC using a chiral column (Condition A) after derivatization of an aliquot with diazomethane to give the corresponding methyl ester) and 35.5% yield. The methyl ester derivative was characterized: $^1H$ NMR (400 MHz, $CDCl_3$) δ8.85 (bs, 1H), 6.55 (s, 1H), 3.66 (s, 3H), 3.17 (m, 1H), 3.05 (m, 1H), 2.84 (m, 1H), 2.57 (m, 1H), 2.41 (m, 1H), 1.6 (s, 9H), 1.4 (s, 9H); MS (FAB) m/z 401.1 $(MH)^+$.

I claim:
1. A process for the preparation of compounds with high enantiomeric purity of formula II:

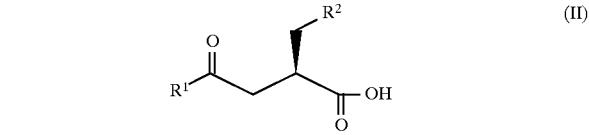

wherein $R^1$ is lower alkoxy and $R^2$ is $CCl=CH_2$, $CBr=CH_2$, 2-amino-4-thiazolyl or 2-(1,1-dimethylethoxy carbonyl)amino-4-thiazolyl, said process comprising:
(i) selectively hydrolyzing one enantiomer of a racemic mixture of an ester of formula III:

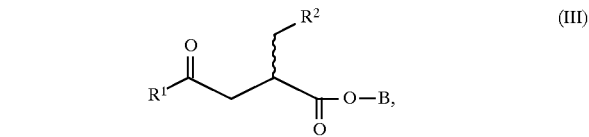

wherein B is lower alkyl, with an effective amount of an esterase selected from Subtilisin Carlsberg or α-chymotrysin, in a reaction medium comprising $H_2O$ or a mixture of $H_2O$ and an $H_2O$ miscible inert organic solvent, in the presence of an alkali metal hydroxide to maintain the pH of the reaction medium at about 7.0 to about 8.5 to form a reaction mixture comprising compounds of formula II (as an alkali metal salt) and formula IIIa

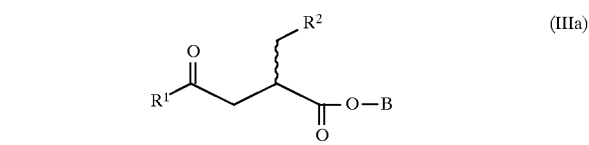

and
(ii) separating from the reaction mixture the compounds of formula II.
2. The process according to claim 1 wherein $R^2$ is $CCl=CH_2$, $CBr=CH_2$ or 2-amino-4-thiazolyl.
3. The process according to claim 2 wherein $R^2$ is $CCl=CH_2$, or $CBr=CH_2$.
4. The process according to claim 1 wherein the esterase is Subtilisin Carlsberg.
5. The process according to claim 1 wherein the reaction medium comprises from about 0 to about 3% (v/v) of a $H_2O$ miscible inert organic solvent.
6. The process according to claim 5 wherein the $H_2O$ miscible inert organic solvent is selected from acetone or acetonitrile.
7. The process according to claim 1 where in the alkali metal hydroxide is NaOH, KOH or LiOH.
8. The process according to claim 1 wherein the hydrolyzation is done at a temperature of about 20° C. to about 55° C.
9. The process according to claim 8 wherein the temperature is about 20° C. to about 37° C.
10. A compound of formula II:

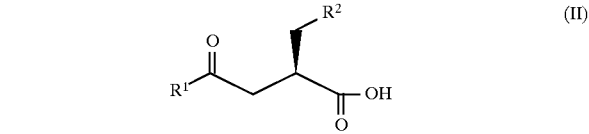

wherein $R^1$ is lower alkoxy and $R^2$ is $CCl=CH_2$, $CBr=CH_2$, 2-amino-4-thiazolyl or 2-(1,1-dimethylethoxy carbonyl)amino-4-thiazolyl.
11. The compound as recited in claim 10 wherein $R^1$ is 1,1-dimethylethoxy and $R^2$ is $CCl=CH_2$, or $CBr=CH_2$.

* * * * *